(12) United States Patent
Tankovich (10) Patent No.: US 12,029,915 B2
(45) Date of Patent: Jul. 9, 2024

(54) LASER SYSTEM FOR MULTIPLE BEAM TISSUE THERAPY WITH TISSUE AND LASER FUNCTIONAL COOLING

(71) Applicant: Nikolai Tankovich, San Diego, CA (US)

(72) Inventor: Nikolai Tankovich, San Diego, CA (US)

( * ) Notice: Subject to any disclaimer, the term of this patent is extended or adjusted under 35 U.S.C. 154(b) by 0 days.

(21) Appl. No.: 16/895,998

(22) Filed: Jun. 8, 2020

(65) Prior Publication Data

US 2021/0052915 A1 Feb. 25, 2021

Related U.S. Application Data

(63) Continuation-in-part of application No. 16/546,267, filed on Aug. 20, 2019, now Pat. No. 10,675,481.

(51) Int. Cl.
| | |
|---|---|
| *A61N 5/06* | (2006.01) |
| *A61B 18/00* | (2006.01) |
| *A61B 18/20* | (2006.01) |
| *A61N 5/00* | (2006.01) |
| *A61N 5/067* | (2006.01) |

(52) U.S. Cl.
CPC .......... *A61N 5/0616* (2013.01); *A61B 18/203* (2013.01); *A61B 2018/00452* (2013.01); *A61N 2005/005* (2013.01); *A61N 2005/007* (2013.01); *A61N 5/067* (2021.08)

(58) Field of Classification Search
None
See application file for complete search history.

(56) References Cited

U.S. PATENT DOCUMENTS

| | | |
|---|---|---|
| 5,807,379 A | 9/1998 | L'Esperance |
| 6,406,474 B1 | 6/2002 | Neuberger |
| 8,251,982 B2 | 8/2012 | Zaghetto |
| 8,444,562 B2 | 5/2013 | Barthe |
| 10,675,481 B1 | 6/2020 | Tankovich |

(Continued)

FOREIGN PATENT DOCUMENTS

| | | |
|---|---|---|
| KR | 10-2008-0004451 A1 | 1/2008 |
| KR | 20080004451 A | 1/2008 |

(Continued)

OTHER PUBLICATIONS

SH Price, "The Peltier Effect and Thermoelectric Cooling" Mar. 26, 2007, Physics 212 Web Project, pp. 1-2 (2007).

(Continued)

*Primary Examiner* — Brian T Gedeon
(74) *Attorney, Agent, or Firm* — TMB Law; Timothy M. Brown (57) ABSTRACT

The invention provides a laser system and method for administering multiple beams of laser energy in tissue treatment applications. The system administers the beams simultaneously in a distribution pattern of spatially separated overlapping and non-overlapping regions on a tissue. The simultaneous administration and distribution pattern permit the beams to propagate within a tissue without producing the light scattering effects that characterize the sequential application of multiple laser beams to a tissue. The laser system can comprise tissue cooling and laser cooling components.

10 Claims, 6 Drawing Sheets

(56) References Cited

U.S. PATENT DOCUMENTS

| | | | |
|---|---|---|---|
| 2003/0100936 A1* | 5/2003 | Altshuler | A61F 7/02 |
| | | | 607/96 |
| 2003/0109860 A1 | 6/2003 | Black | |
| 2004/0039312 A1 | 2/2004 | Hillstead | |
| 2006/0004306 A1 | 1/2006 | Altshuler | |
| 2006/0084953 A1 | 4/2006 | Tankovich | |
| 2006/0095096 A1 | 5/2006 | DeBenedictis | |
| 2006/0116669 A1* | 6/2006 | Dolleris | A61B 18/203 |
| | | | 606/17 |
| 2006/0161142 A1 | 7/2006 | Sierra | |
| 2007/0208326 A1* | 9/2007 | Connors | A61B 18/203 |
| | | | 606/9 |
| 2007/0244526 A1 | 10/2007 | Zaghetto | |
| 2008/0125835 A1* | 5/2008 | Laurent | A61N 5/0617 |
| | | | 607/89 |
| 2008/0132886 A1 | 6/2008 | Cohen | |
| 2008/0161888 A1 | 7/2008 | Hsia | |
| 2008/0294152 A1 | 11/2008 | Altshuler | |
| 2009/0118720 A1 | 5/2009 | Black | |
| 2010/0082019 A1 | 4/2010 | Neev | |
| 2012/0209257 A1 | 8/2012 | van der Weide | |
| 2013/0096546 A1 | 4/2013 | Mirkov | |
| 2013/0103017 A1 | 4/2013 | Weckwerth | |
| 2014/0058227 A1 | 2/2014 | Yamanaka | |
| 2015/0174424 A1* | 6/2015 | Pryor | A61N 5/0619 |
| | | | 601/18 |
| 2015/0224332 A1* | 8/2015 | Hewitson | A61N 5/06 |
| | | | 607/89 |
| 2017/0304645 A1* | 10/2017 | Schomacker | A61N 1/40 |
| 2018/0296269 A1 | 10/2018 | Bhawalkar | |
| 2019/0025212 A1 | 1/2019 | Evans | |
| 2021/0316155 A1* | 10/2021 | Vahlensieck | A61B 18/203 |

FOREIGN PATENT DOCUMENTS

| | | | |
|---|---|---|---|
| RU | 2113827 C1 | 6/1998 | |
| RU | 120008 U1 | 10/2012 | |
| RU | 137201 U1 | 9/2013 | |
| WO | 2018106751 A1 | 6/2018 | |
| WO | WO-2019241465 A1 * | 12/2019 | A61B 18/203 |

OTHER PUBLICATIONS

Copending U.S. Appl. No. 16/552,517 by Tankovich; Title: Tip for Multiple Beam Tissue Therapy; filed Aug. 27, 2019.

Extended European Search Report for Copending European Application No. 19207702.0, dated Dec. 5, 2020.

Reasons for Rejection for Copending South Korean Application No. 10-2019-0170728, dated Mar. 31, 2021.

Office Action for Copending S. Korea Application No. 10-2019-0170728, dated Mar. 31, 2021.

Office Action for Copending Russia Application No. 2020127609, dated Feb. 16, 2021.

Smith, Fibroblasts as sentinel cells. Synthesis of chemokines and regulation of inflammation, American Journal of Pathology, vol. 151, No. 2, Aug. 1997.

* cited by examiner

LASER SYSTEM FOR MULTIPLE BEAM TISSUE THERAPY WITH TISSUE AND LASER FUNCTIONAL COOLING

CROSS-REFERENCE TO RELATED APPLICATIONS

This application is a continuation-in-part of application Ser. No. 16/546,267 filed Aug. 20, 2019, now U.S. Pat. No. 10,675,481, the entire contents of which are incorporated herein by reference for all purposes.

FIELD OF THE INVENTION

The invention relates to therapeutic electromagnetic radiation systems, and in particular, laser systems for use in tissue therapy.

BACKGROUND OF THE INVENTION

There are no lasers or laser handpieces on the market today that can simultaneously deliver two or more wavelengths of laser energy in spacial, fractional form. There are fractional lasers that can deliver one wavelength of laser energy. However, laser treatment usually requires different modalities of energy in order successfully treat the pathologies to which they are applied, such as skin pathologies. For example, the treatment of dermal rhytides from solar elastosis requires both deep and superficial laser effects on the skin to induce the skin to release therapeutic cytokines from the skin compartments, including the reticular dermis and papillary dermis. However, the sequential application of multiple wavelengths of laser energy compromises the treatment. The irradiation of the skin with a first wavelength of laser energy modifies the skin by coagulating tissue within the skin and causing it to swell. These effects alter the propagation of laser light within the skin such that the coagulated and swollen skin will swallow and scatter a second wavelength of laser energy that is subsequently applied in an effort to treat the skin. Moreover, the treated, swollen skin layer is inhibited in its ability to absorb therapeutic cytokines that are released by laser damage. The deficiencies of the sequential application of multiple laser wavelengths are even greater if one of the wavelength's energy beam is absorbed by water in the tissue, as is the case with laser wavelengths of 3, 5 and 10 micrometers.

Another example of the problems associated with the sequential application of different wavelengths of laser energy is provided by laser therapy of skin telangiectasias. Contemporary laser treatments for skin telangiectasias involve the application of a first laser system that emits a laser wavelength ranging between 528 nm to 595 nm to coagulate red blood vessels (i.e. small size telangiectasia), and the subsequent application of a second laser system that emits a laser wavelength ranging between 810 nm and 1080 nm to coagulate blue blood vessels (i.e. large size telangiectasia). Thus, current laser treatments for skin telangiectasias require the use of separate laser therapy systems having different wavelengths to coagulate both red and blue blood vessels in the skin, making the treatments inefficient, complicated, and costly.

What is needed in the art therefore is an effective laser therapy system that can simultaneously deliver multiple wavelengths of laser energy through the use of a single laser unit without producing interference between the wavelengths within the treated tissue.

SUMMARY OF THE INVENTION

The invention provides a therapeutic laser system that simultaneously delivers multiple wavelengths of laser energy using a single unit in a single application. The laser system delivers multiple wavelengths of laser energy without producing interference between the wavelengths that typically results when a tissue is treated with multiple wavelengths of laser energy in separate applications. The invention can avoid interference of the wavelengths by delivering the wavelengths simultaneously and in spatially separated and overlapping regions of the tissue being treated. By delivering the wavelengths simultaneously, the effects of multiple wavelengths of laser energy are produced in the tissue instantaneously thereby eliminating the need for a separate application of a subsequent wavelength which would necessarily be compromised by the earlier application of the preceding treatment wavelength. In addition, the laser system of the invention can spatially separate the wavelength beams on the treated tissue such that two wavelengths of laser energy are not applied to the same region of tissue thereby preventing a treated tissue from interfering with the propagation of a second wavelength of laser treatment. Spatial separation of multiple wavelengths of laser energy also permits the laser energy to penetrate tissues in different regions and at different depths thereby stimulating the tissues to release different therapeutic cytokines in different locations within the same tissue.

REFERENCE NUMBERS

1—Laser system
2—Power supply

3—Tip
4—Display
5—Laser
5.1—Beam from laser 5
5.2—Beam distribution pattern of beam 5.1
5.3—Propagation profile of beam 5.1
6—Laser
6.1—Beam of laser 6
6.2—Beam distribution pattern of beam 6.1
6.3—Beam propagation profile of beam 6.1
7—Fractional scanner for laser 6
8—Fractional scanner for laser 5
9—Power cord
10—Microwaves
11—Microwave generator
12—Microwave conductor
13—Intense pulsed light source
14—Fiber optic conductor
15—Non-coherent light
16—Ultrasound transducer
17—Ultrasound waves
18—Ultrasound transducer power supply
19—Power cord
20—Skin
CK1—Cytokines released laser 6.1
CK2—Cytokines released by laser 5.1
CK3—Cytokines released by the overlap of beams 5.1 and 6.1
21—Tissue cooling module
22—Tissue cooling module outer wall
23—Tissue cooling module inner wall
24—Tissue cooling module conduit
25—Fluid reservoir
26—Fluid pump
27—Feed conduit
28—Return conduit
29—Thermal sink
30—Laser cooling module
31—Cooling fan

DEFINITIONS

As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length.

As used herein, the phrase "skin condition" refers to a condition or disorder affecting the skin, including, without limitation, wrinkles, loss of skin elasticity, skin photoaging, scars, rhytides, acne, telangiectasia, vitiligo, skin lesions, tattoo removal, blepharoptosis, and combinations thereof.

As used herein, the phrase "skin lesion" refers to benign growths and lesions (e.g. actinic keratosis), neoplastic lesions (e.g. melanoma, basal cell carcinoma, and squamous cell carcinoma), skin wounds (e.g. burns, surgical wounds, cuts, and abrasions), diabetic ulcers, and bed sores.

As used herein, the terms "treat," "treating," and "treatment" can refer to the clinical intervention of a disease or condition in an attempt to alter, alleviate, ameliorate, prevent, lessen or reverse the progression or symptoms of the disease or condition.

As used herein, the phrase "cytokine profile" refers to the cytokines, chemokines, and other biomolecules that are released from a tissue or collection of cells that results from contacting the tissue or collection of cells with laser energy. The contact can result in the tissue or collection of cells being ruptured, cauterized, heated, or otherwise damaged. Cytokine profiles can be released from skin one or more skin structures, such as the epidermis, papillary dermis, and dermis.

DETAILED DESCRIPTION

The invention relates to a laser system and method for delivering multiple wavelengths of laser energy in the treatment of tissue conditions, such as conditions of the skin. The laser system delivers multiple wavelengths of laser energy without the wavelengths interfering with one another in the tissues to which they are applied. The laser system can avoid interference of the wavelengths by simultaneously delivering overlapping and non-overlapping wavelengths in spatially separated areas of application.

Figure 1:
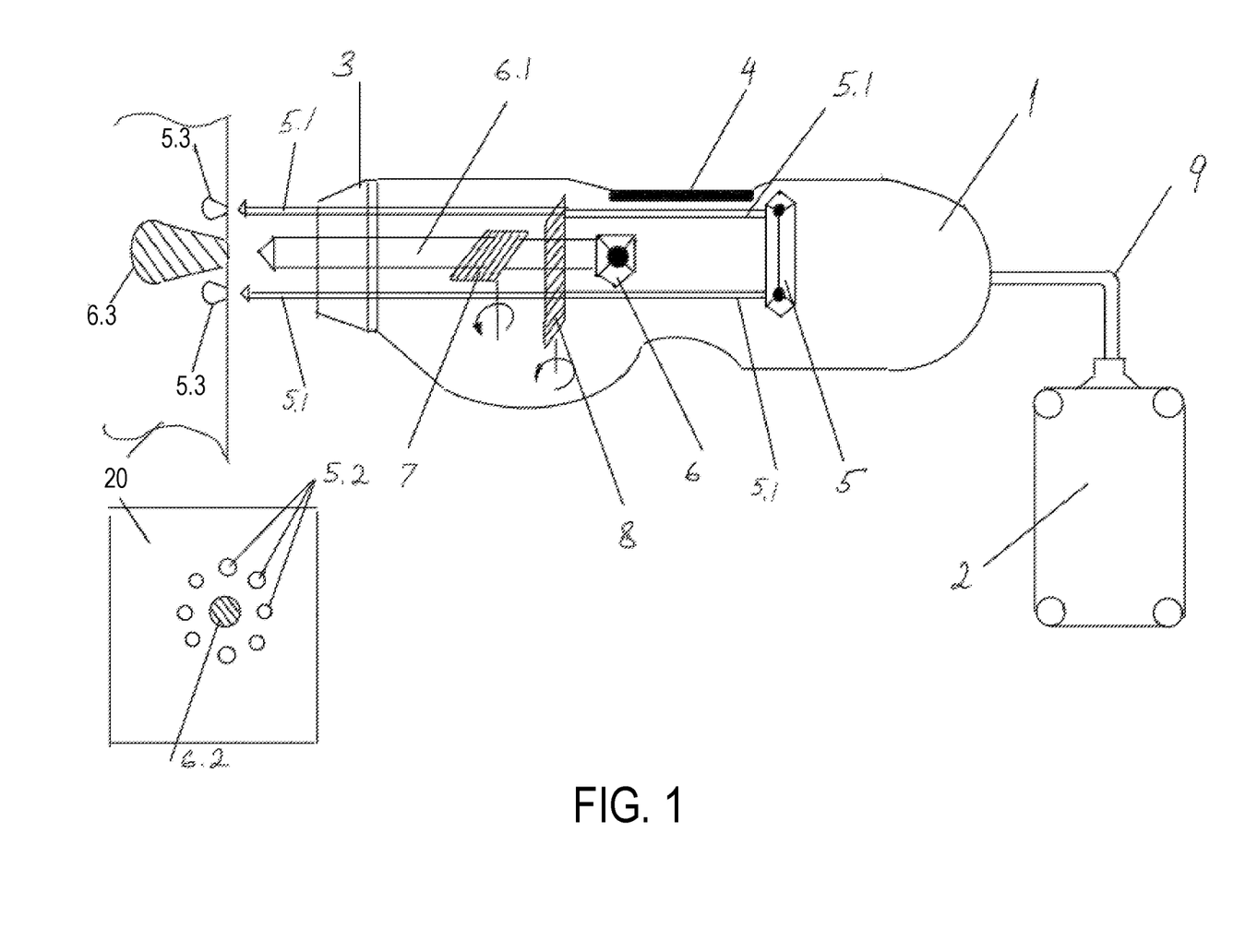
FIG. 1 shows an embodiment of the laser system of the invention.

FIG. 1 depicts an embodiment of the laser system of the invention. In this embodiment, laser system 1 is in electrical communication with power supply 2 through power cord 9. Laser system 1 has laser 5 that generates beam 5.1, and laser 6 which generates beam 6.1. Laser 5 and laser 6 can be solid-state lasers, laser diode lasers (e.g. diode pumped fiber lasers and diode pumped Tm-doped fiber lasers), gas lasers, chemical lasers, dye lasers, metal-vapor lasers, semiconductor lasers, or combinations thereof. For example, laser 5 can be a laser diode, and laser 6 can be a solid-state laser. Alternatively, laser 5 and laser 6 can be the same type of laser. For example, laser 5 and laser 6 can be a pair of gas lasers, a pair of laser diodes, or a pair of solid state lasers. In some aspects of the invention, laser 5 and laser 6 are dermatological lasers, ophthalmic lasers, surgical lasers, or cosmetic lasers. Laser 5 and laser 6 can be a combination of lasers comprising a diode pumped Tm-doped fiber laser and a solid state Er:YSGG laser. In some aspects of the invention, laser 5 and laser 6 are laser diodes or diode pumped fiber lasers. The laser diodes can individually have a power of one thousandth of a Watt, one hundredth of a Watt, one tenth of a Watt, half a Watt, one Watt, one dozen Watts, two dozen Watts, three dozen Watts, four dozen Watts, five dozen Watts, six dozen Watts, seven dozen Watts, or more. Laser 5 and laser 6 can generate lasers in pulse beam mode, continuous beam mode, or a combination thereof. For example, laser 5 can generate beam 5.1 in pulse mode, while laser 6 generates beam 6.1 in continuous mode. The pulse beam mode can produce a pulse having a duration from about a dozen femtoseconds to about one or more seconds. In some aspects of the invention, laser system 1 is a laser handpiece.

In at least one aspect of the invention, beam 5.1 and beam 6.1 have different wavelengths. Beam 5.1 and beam 6.1 can have different wavelengths selected from about 540 nm, about 700 nm, about 810 nm, about 980 nm, about 1064 nm, about 1300 nm, about 1440 nm, about 1450 nm, about 1550 nm, about 1927 nm, about 1940 nm, about 2790 nm, about 2790 nm, about 2940 nm, and about 10600 nm. Non-limiting pairings for the wavelengths of beam 5.1 and beam 6.1, include, but are not limited to about 1550 nm and about 1930 nm, about 980 nm and about 1550 nm, about 980 nm and about 1930 nm, about 810 nm and about 1030 nm, about 1440 nm and about 1930 nm, about 532 nm and about 540 nm, about 532 nm and about 980 nm, about 1927 nm and about 1440 nm, about 577 nm and about 980 nm, and about 540 nm and about 980 nm. In at least one aspect of the invention, beam 5.1 and beam 6.1 can have the same wavelength, including without limitation the wavelengths disclosed herein. The wavelengths for the beams can be selected based on their ability to propagate within a tissue or group of cells that is desired to be illuminated with laser energy, it being understood that chromatophores selectively absorb certain wavelengths of laser energy.

Laser system 1 includes fractional scanner 7 which is in optical communication with laser 6 to distribute beam 6.1, and fractional scanner 8 which is in optical communication with laser 5 to distribute beam 5.1. In some aspects of the invention, fractional scanners 7 and 8 are optical laser mirrors in mechanical communication with scanner motors (not shown) that are adapted to move the mirrors in a manner that reflects the mirrors' respective beams to produce a desired distribution pattern of laser light. The motors are adapted to receive instructions from a processor (not shown) within laser system 1 for executing a pattern of movement that moves scanners 7 and 8 in a manner that reflects and distributes beams 5.1 and 6.1 in a desired distribution pattern of laser light. For example, fractional scanner 7 can be moved by its motor according to a first pattern that reflects beam 6.1 to achieve beam distribution pattern 6.2, while fractional scanner 8 can be moved by its motor according to a second pattern that reflects beam 5.1 to achieve beam distribution pattern beam 5.2. Fractional scanners 7 and 8 can control the number of distribution spots for the beams, wherein greater motor speeds provide a greater number distribution spots, and slower motor speeds providing fewer distribution spots. Fractional scanner 7 and fractional scanner 8 can be moved by their respective motors to distribute beams 5.1 and 6.1 in a pattern selected from overlapping beams, partially overlapping beams, non-overlapping beams, and combinations thereof. In some aspects of the invention, the scanner motors are substituted with one or more solenoids, one or more magnetic coils, or a combination thereof.

In some aspects of the invention, scanners 7 and 8 are beam separation windows having a pair of opposing planar surfaces. The beam separation windows can be made of sapphire, thermoconductive glass, or other material suitable for transmitting laser light. The beam separation windows can be arranged within laser system 1 such that beams 5.1 and 6.1 contact the beam separation windows in an orientation that is perpendicular, or generally perpendicular, to the planar surfaces of the windows. Each beam separation window comprises a coating on at least one planar surface that blocks the transmission of laser energy. The coatings can be blocking for one or more wavelengths of laser energy. Suitable materials for the coating include, but are not necessarily limited to, evaporated metal films (e.g. aluminum and/or gold), silica, scandium oxide, magnesium fluoride, hafnium fluoride, or combinations thereof. The coatings have one or more openings that permit at least a portion of a laser beam to be transmitted through the beam separation windows to produce a desired beam distribution pattern. For example, the beam separation window of scanner 7 can have a plurality of openings in the coating to split beam 5.1 into a plurality of beams, while the beam separation window of scanner 8 comprises a single opening in its coating to constrict beam 6.1 to a beam having a smaller cross-section. In such configurations, it will be understood that lasers 5 and 6 generate their respective beams with a cross section that is sufficiently large to cover at least a portion of the openings in the coatings on the windows. The openings in the windows can be arranged to transmit beams 5.1 and 6.1 in a beam distribution pattern selected from overlapping beams, partially overlapping beams, non-overlapping beams, and combinations thereof. The openings in the coatings can be arranged to produce the various configurations for beam distribution pattern 5.2 and beam distribution pattern 6.2 as disclosed herein.

FIG. 1 depicts a non-limiting beam distribution pattern on skin 20 of a patient wherein fractional scanner 8 is adapted to distribute beam 5.1 according to beam distribution pattern 5.2, and fractional scanner 7 is adapted to distribute beam 6.1 according to beam distribution pattern 6.2, such that beams 5.1 contacts skin 20 in a pattern that surrounds the areas of skin 20 that are contacted by beam 6.1. In this pattern, beams 5.1 and 6.1 contact skin 20 in a spatially separated, non-overlapping areas. The side view of skin 20 shows beam propagation profile 5.3 indicating that beam 5.1 can propagate deeper within skin 20 than beam propagation profile 6.3 of beam 6.1. The side view of skin 20 further shows that the areas of skin 20 where the beams propagate are spatially separated and non-overlapping.

Figure 2A:
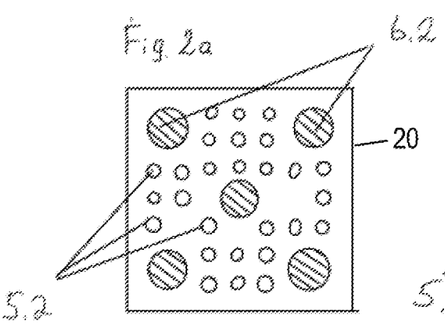
FIG. 2A shows a cross-section of a non-limiting, non-overlapping beam distribution pattern provided by the laser system of the invention.
Figure 2B:
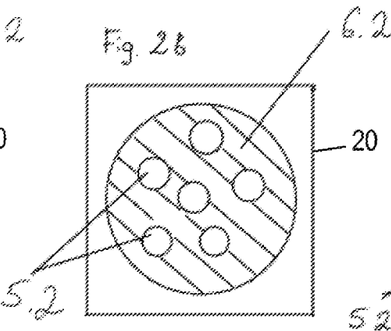
FIG. 2B shows a cross-section of a non-limiting, fully overlapping beam distribution pattern provided by the laser system of the invention.
Figure 2C:
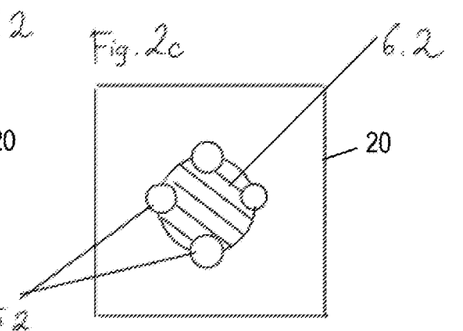
FIG. 2C shows a cross-section of a non-limiting, partially overlapping beam distribution pattern provided by the laser system of the invention.
Figure 2D:
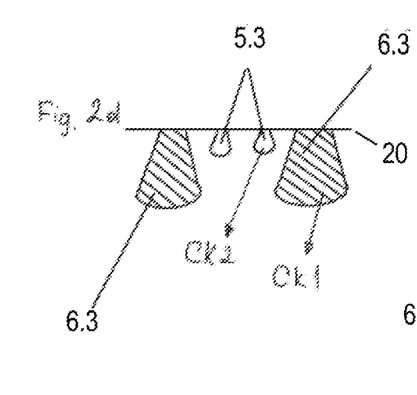
FIG. 2D is a side view of the beam distribution of pattern of FIG. 2A showing the effects of the simultaneous application of non-overlapping wavelengths of laser energy in a tissue.

Fractional scanner 7 and fractional scanner 8 can be adapted to provide other beam distribution patterns, such as the non-limiting patterns depicted in FIGS. 2A, 2B, and 2C. FIG. 2A depicts a planar view of skin 20 wherein scanner 8 distributes beam 5.1 according to beam distribution pattern 5.2, and scanner 7 distributes beam 6.1 according to beam distribution pattern 6.2 such that beam 5.1 contacts skin 20 in spatially separated spots interspersed between the spots contacted by beam 6.1 without overlapping of the beams. FIG. 2D is a side view of skin 20 from FIG. 2A depicting the propagation of beams 5.1 and 6.1 in the skin, wherein beam propagation profile 5.3 shows beam 5.1 does not propagate as deeply as the beam propagation profile of beam 6.1, and that beam propagation profiles 5.3 and 6.3 do not overlap within skin 20. In some aspects of the invention, beam 5.1 can have a wavelength of about 1927 nm, wherein beam propagation profile 5.3 occupies only the epidermis at a depth of between about 30 microns and 50 microns, while beam 6.1 can have a wavelength of about 1550 nm, wherein beam propagation profile 6.3 occupies the papillary dermis at a depth of between about 150 microns and 200 microns.

FIG. 2D also depicts the release of cytokine profile CK2 from the area of skin 20 that is occupied by beam propagation profile 5.3, and the release of cytokines CK1 from the area of skin that is occupied by beam propagation profile 6.3. Without being limited to any particular theory or mechanism, contacting tissues, such as skin, with laser light can create zones of damage in the areas where the laser light propagates in the tissue, leading the damaged tissue to release cytokines which migrate from the zone of damage to produce a therapeutic effect in the surrounding, undamaged tissue. For example, contacting the skin with wavelength of laser energy that propagates within the epidermis can create a zone of damage in this tissue compartment leading to the release of a first cytokine profile, while contacting the skin with a second wavelength of laser energy that propagates in the papillary dermis can create a zone of damage in this tissue compartment leading to the release of a second cytokine profile.

Figure 2E:
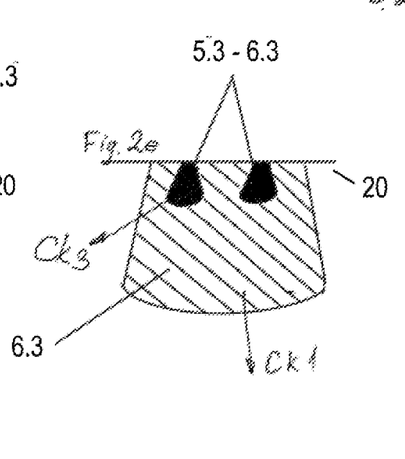
FIG. 2E is a side view of the beam distribution of pattern of FIG. 2B showing the effects of the simultaneous application of fully overlapping wavelengths of laser energy in a tissue.

FIG. 2B depicts a planar view of skin 20 wherein scanner 8 distributes beam 5.1 according to beam distribution pattern 5.2 and scanner 7 distributes beam 6.1 according to beam distribution pattern 6.2, such that beam 5.1 overlaps beam 6.1 on skin 20. FIG. 2E is a side view of skin 20 from FIG. 2B depicting the propagation of beams 5.1 and 6.1 in the skin, wherein propagation profile 6.3 shows that beam 6.1 propagates more deeply than beam 5.1 in the region of skin depicted by beam propagation profile 5.3-6.3 where beams 5.1 and 6.1 overlap. FIG. 2E shows the release of cytokines CK1 from the area of skin 20 that is occupied by beam propagation profile 6.3 and the release of cytokines CK3 from the area of skin 20 that is occupied by beam propagation profile of 5.3-6.3. In some aspects of the invention, the beam propagation profiles of FIG. 2E can be such that beam 5.1 is produced by an Er:YSGG solid-state laser at a wavelength of about 2790 nm, wherein beam propagation profile 5.3 occupies the epidermis at a depth between about 10 microns and about 30 microns, and beam 6.1 has a wavelength of about 1550 nm wherein beam propagation profile 6.3 occupies the papillary dermis at a depth between about 150 microns and about 200 microns. In such an aspect, it will be understood that cytokine profile CK1 will be produced by beam 6.1 damaging the papillary dermis, and cytokine profile CK3 will be produced by beams 5.1 and 6.1 damaging the epidermis.

Figure 2F:
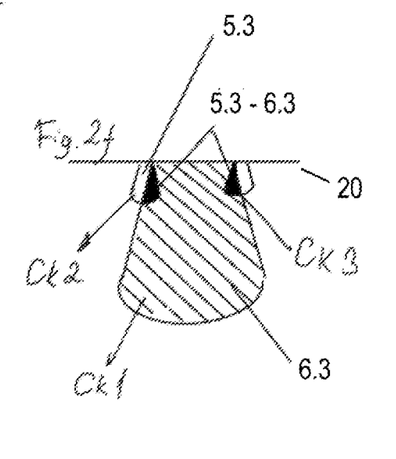
FIG. 2F is a side view of the beam distribution of pattern of FIG. 2C showing the effects of the simultaneous application of partially overlapping wavelengths of laser energy in a tissue.

FIG. 2C depicts a planar view of skin 20 wherein scanner 8 is adapted to distribute beam 5.1 according to beam distribution pattern 5.2 and scanner 7 is adapted to distribute beam 6.1 according to beam distribution pattern 6.2. In such a configuration, a portion of beam 5.1 overlaps beam 6.1. FIG. 2F is a side view of skin 20 from FIG. 2C depicting the propagation of beams 5.1 and 6.1 in the skin wherein beam propagation profile 6.3 shows beam 6.1 propagates more deeply than beam 5.1. Beam propagation profile 5.3-6.3 depicts a region of skin wherein overlapping beams 5.1 and 6.1 both propagate within skin 20. FIG. 2F shows the release of cytokine profile CK1 from beam propagation profile 6.3, the release of cytokine profile CK2 from beam propagation profile 5.3, and the release of cytokine profile CK3 from beam propagation profile 5.3-6.3. The beam propagation profiles depicted in FIG. 2F can be produced by laser system 1 having a configuration wherein laser 5 is laser diode that produces beam 5.1 at a wavelength of about 1440 nm, and laser 6 is a laser diode that produces beam 6.1 at a wavelength of between about 810 nm and about 980 nm. This configuration can produce beam propagation profile 5.3 and beam propagation profile 5.3-6.3 wherein beam 5.1 propagates within the papillary dermis at a depth of between about 120 microns and about 180 microns, and beam propagation profile 6.3 wherein beam 6.1 propagates within all dermal layers of the skin at a depth between about 4 mm and about 5 mm.

In some aspects of the invention, laser system 1 comprises tip 3. Tip 3 can be a disposable unit that detachably connects to laser system 1. Tip 3 can have one or more reservoirs adapted to contain cosmetics, therapeutic compositions, or combinations thereof. Tip 3 can be adapted to contain compositions including, but not necessarily limited to, drugs (e.g. Avastin™ and Lucentis™), anti-angiogenic antibodies, hyaluronic acid, Botox™, fibroblasts, stem cells, stem cell factors, vitamins, antioxidants, and combinations thereof.

In some aspects of the invention, the laser system includes a display for inputting operation parameters and displaying system feedback. FIG. 1 depicts laser system 1 with display 4 for communicating with a processor within laser system 1 (not shown). Display 4 is configured to display information relating to the operation of laser system 1, such as the power of beams 5.1 and 6.1, the wavelengths of beams 5.1 and 6.1, the pulse duration of the beams, and the number of laser pulses and the amount of laser energy delivered. Display 4 can be configured to receive input from a user, such input including turning laser system 1 on and off, selection of a desired power for each of beams 5.1 and 6.1, the laser mode for the lasers (e.g. pulse or continuous mode), and the duration of the beam pulses, for example.

Figure 3:
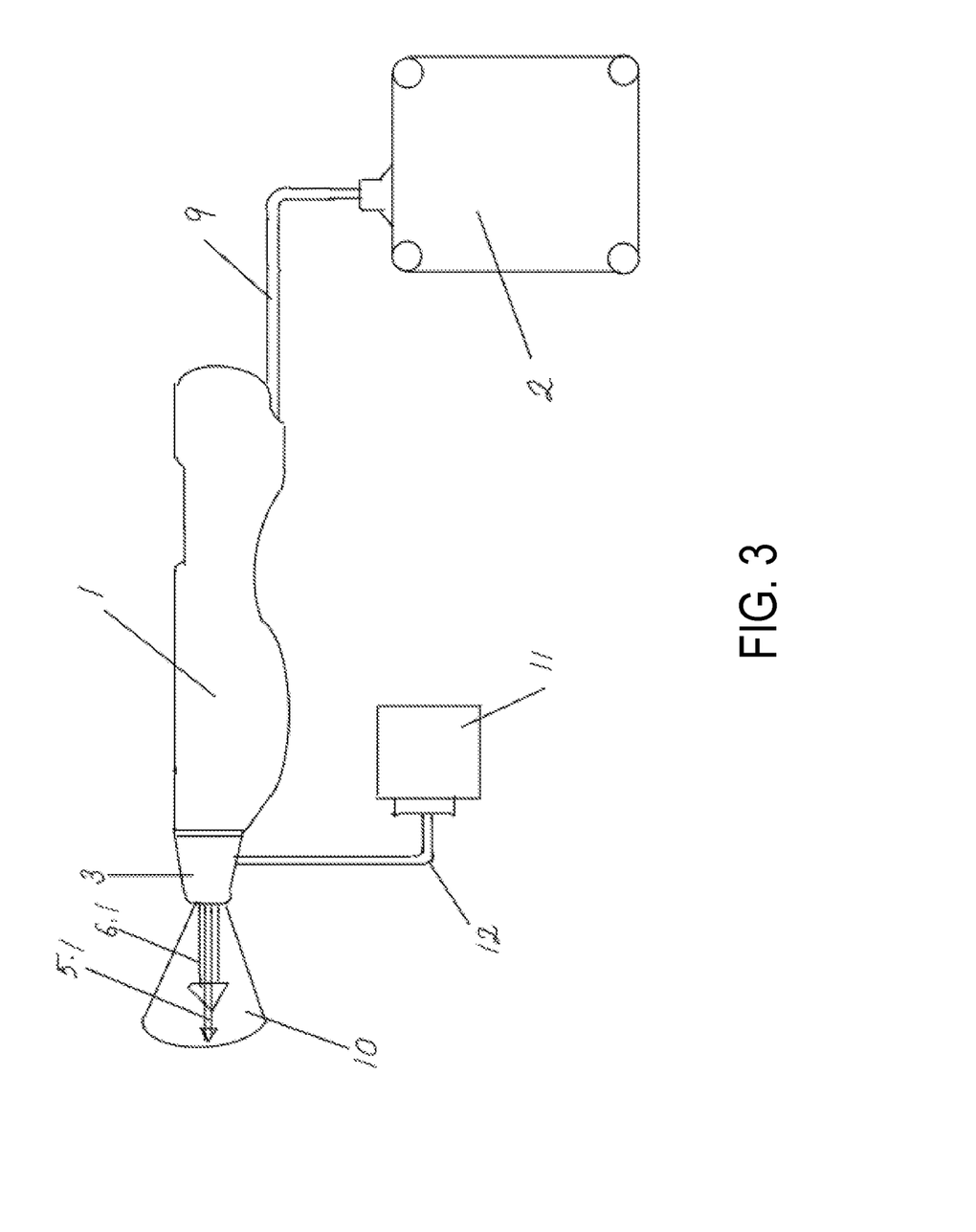
FIG. 3 shows an embodiment of the laser system of the invention having a tip adapted to emit microwave radiation.

FIG. 3 depicts a non-limiting embodiment of the invention wherein laser system 1 comprises tip 3 which is adapted to emit microwave energy. In this embodiment, tip 3 is in electronic communication with microwave generator 11 through microwave conductor 12 such that laser unit 1 is adapted to simultaneously administer microwaves 10, beam 5.1, and beam 6.1 onto a treated tissue, such as the skin of a patient, for example. It will be understood that in this embodiment, display 4 is adapted to monitor and control the operation of microwave generator 11. In some aspects, laser system 1 comprises an integrated microwave generator housed within the system rather than in the tip.

Figure 4:
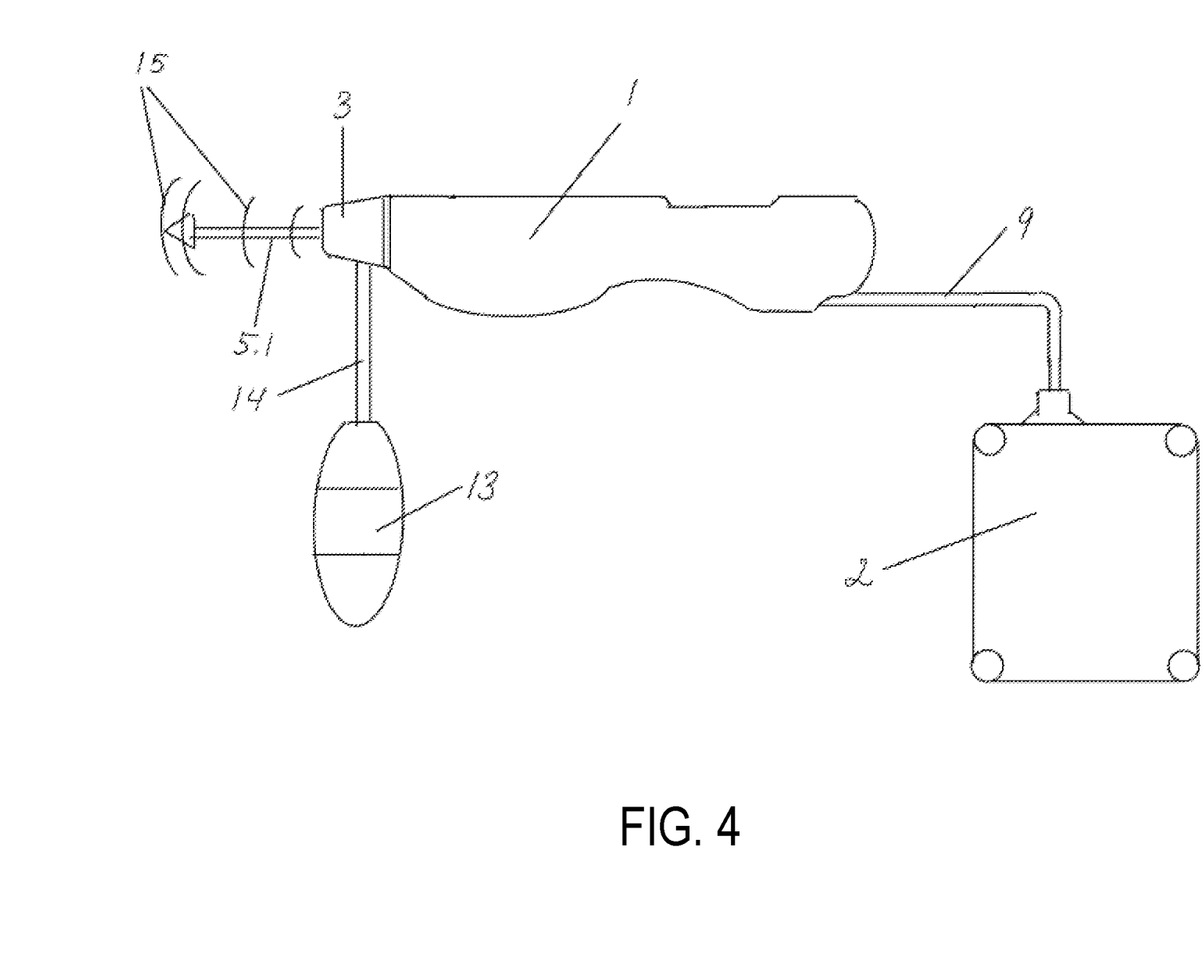
FIG. 4 shows an embodiment of the laser system of the invention having a tip adapted to emit non-coherent light.

FIG. 4 depicts a non-limiting embodiment of the invention wherein laser system 1 comprises tip 3 which is adapted to emit intense pulsed light. In this embodiment, tip 3 is in optical communication with intense pulsed light source 13 through fiber optic conductor 14 such that laser unit 1 is adapted to simultaneously administer non-coherent light 15, beam 5.1, and beam 6.1 onto a treated tissue, such as the skin of a patient, for example. It will be understood that in this embodiment display 4 is adapted to monitor and control the operation of intense pulsed light source 13. In some aspects, laser system 1 comprises an integrated intense pulsed light source housed within the system rather than in the tip.

Figure 5:
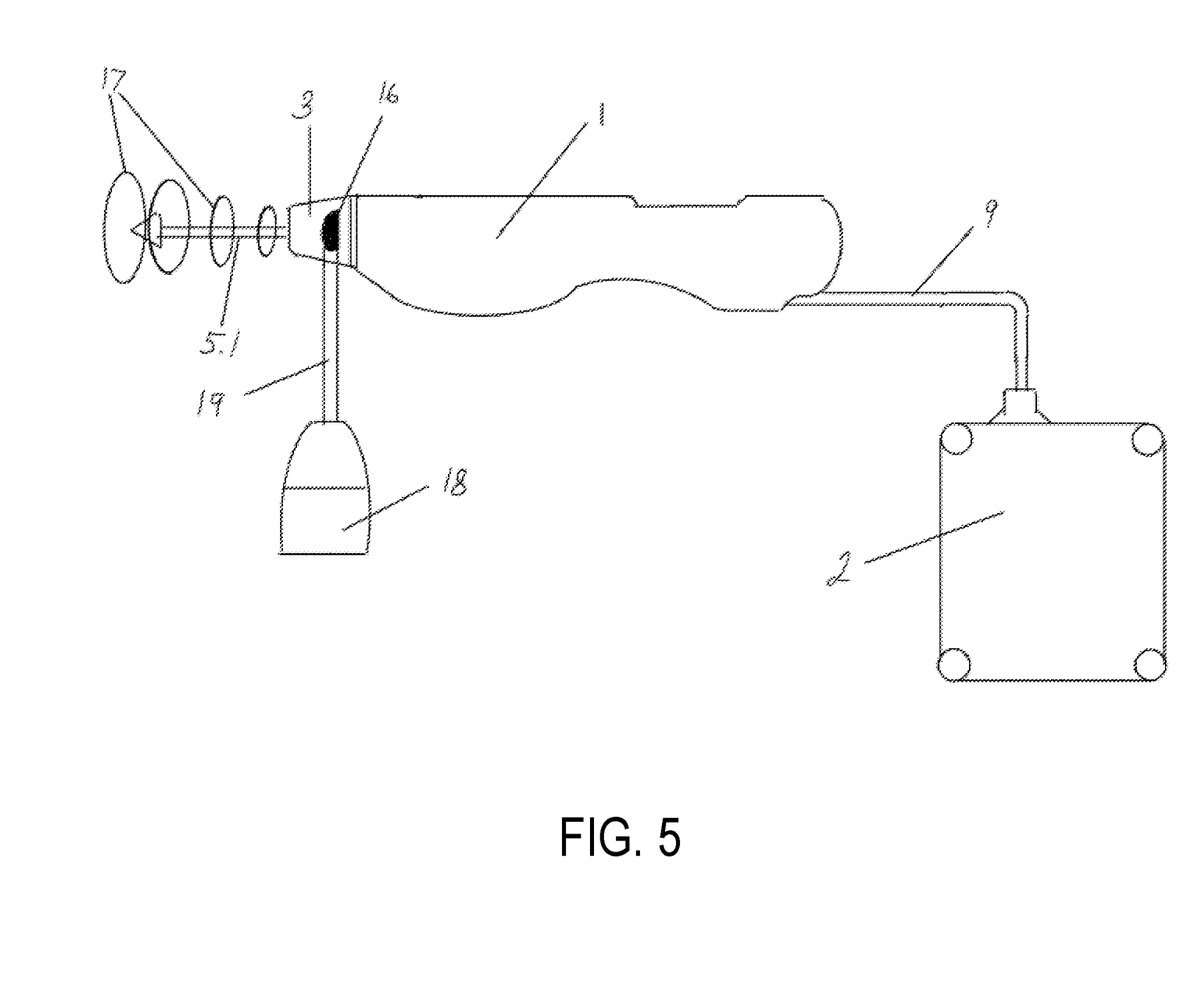
FIG. 5 shows an embodiment of the laser system of the invention having a tip adapted to emit ultrasonic energy.

FIG. 5 depicts a non-limiting embodiment of the invention wherein laser system 1 comprises tip 3 which is adapted to emit ultrasound. In this embodiment, tip 3 comprises ultrasound transducer 16 which is in electronic communication with ultrasound transducer power supply 18 through power cord 19. In this embodiment, laser unit 1 is adapted to simultaneously administer ultrasound waves 17, beam 5.1, and beam 6.1 (not shown) onto a treated tissue, such as the skin of a patient, for example. It will be understood that in this embodiment display 4 is adapted to monitor and control the operation of ultrasound transducer 16. In some aspects, laser system 1 comprises an integrated ultrasound transducer housed within the system rather than in the tip.

In some embodiments, the invention provides a laser system having features for cooling at least one of the tissue of a patient and the lasers within the system. Contemporary laser treatment systems are deficient in that they are limited in the amount of laser energy that can be applied to a patient. This results from the fact that the current required to power high energy laser sources generates significant heat. The generation of significant heat can result in failure of the lasers (e.g. laser diodes), reduced laser life, and can prevent the system from being handled by a user. The inventor discovered a laser system that can cool laser energy sources thereby permitting more powerful lasers to be used in the treatment of tissues while extending laser life. The inventor further discovered a system that permits cooling of the tissue of a patient such that high energy laser sources can be used without producing pain or excessive tissue damage. High energy laser sources provide a system capable of treating deeper tissue layers, such as all layers of the skin.

Figures 6A, 6B:
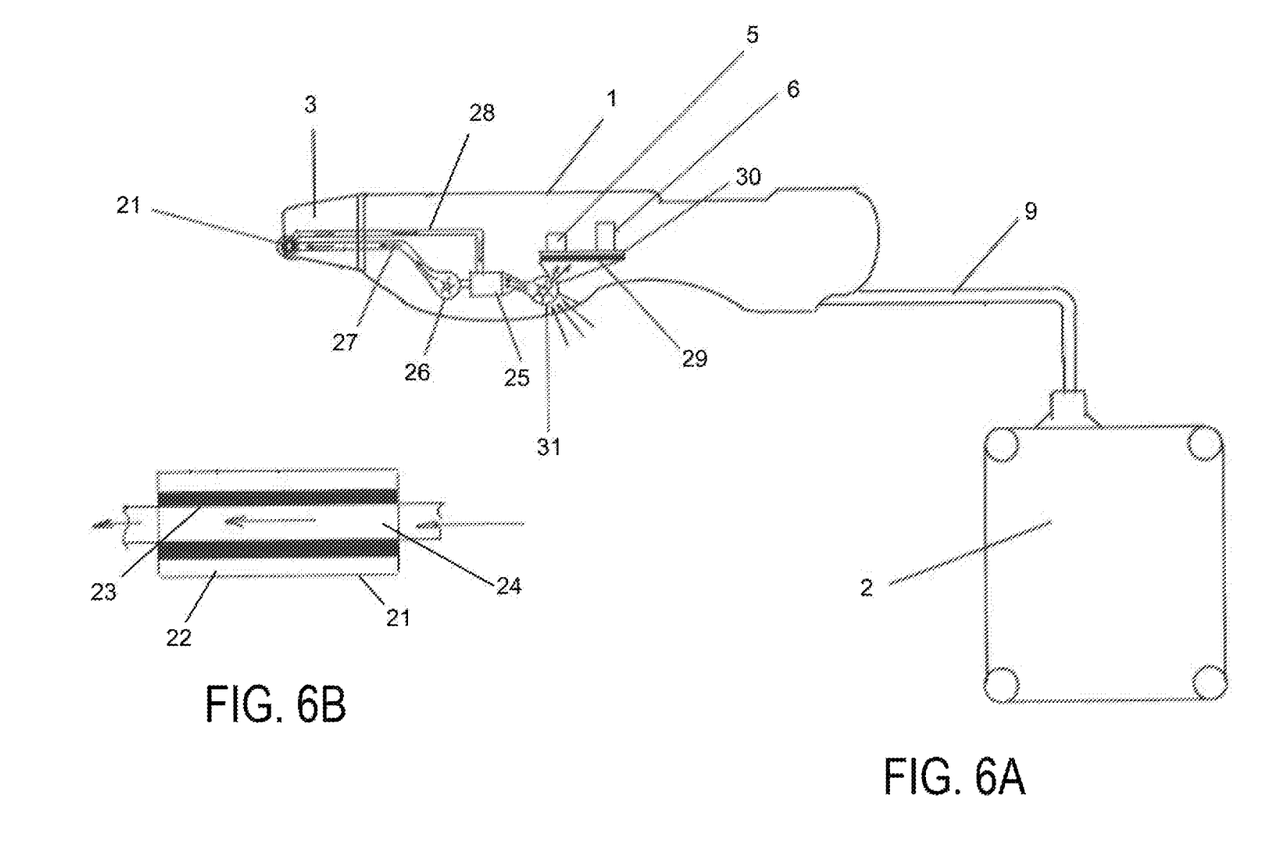
FIG. 6A shows an embodiment of the laser system of the invention having a tissue cooling module and laser cooling module.
FIG. 6B shows a longitudinal, cross-sectional view of the tissue cooling module shown in FIG. 6A.

FIG. 6A shows a non-limiting embodiment of a laser system having features adapted to cool at least one of the tissue of a patient and laser energy sources within the system. Laser system 1 can be electronically connected to power supply 2 by power cord 9. Laser system 1 can feature at least one of laser 5 and laser 6. Laser 5 and laser 6 can be in thermal communication with laser cooling module 30 which is adapted to cool at least one of laser 5 and laser 6. Laser system 1 can feature one or a plurality of laser cooling module 30. Laser cooling module 30 can assume any device or configuration that is capable of reducing the operating temperature of laser 5 and laser 6. In some embodiments, laser cooling module 30 comprises one or more printed circuit boards, one or more Peltier coolers, one or more thermoelectric plates, or combinations thereof. In some embodiments, laser cooling module 30 is made from a thermoelectric material, such as tellurium, for example. Laser 5 and laser 6 can be individually in thermal communication with one or a plurality of laser cooling module 30. Laser cooling modules for use with the invention can be obtained from, for example, TECA (Chicago, IL), Custom Thermoelectric (Bishopville, MD), TE Technologies (Traverse City, MI).

Laser cooling module 30 is in thermal communication with thermal sink 29 which is adapted to conduct heat away from at least one of laser cooling module 30, laser 5, and laser 6. Thermal sink 29 can be a thermal conductive material such as aluminum, an aluminum alloy, copper, or combinations thereof. Thermal sink 29 can assume a finned configuration. Thermal sink 29 can be in communication with cooling fan 31. Cooling fan 31 can be adapted to draw air into laser system 1 through at least one opening in the system's housing (not shown) and blow air against thermal sink 29 thereby dissipating heat away from at least one of laser cooling module 30, laser, 5 and laser 6. Air flow into laser system 1 and against thermal sink 29 is depicted by arrows in FIG. 6A. Laser system 1 can be a laser system as disclosed herein.

Still referring to FIG. 6A, laser system 1 can function to cool the tissue of a patient to which laser energy is applied. In some such embodiments, laser system 1 features tissue cooling module 21 which can be detachably connected to laser system 1 by tip 3. In other embodiments, tissue cooling module 21 is connected directly to a housing which encases the components of laser system 1. Tissue cooling module 21 can assume the shape of a cylindrical body that is adapted to rotate when dragged across a tissue of a patient. In some embodiments, tissue cooling module 21 is a fixed body that is not adapted to rotate.

Features of tissue cooling module 21 are depicted by FIG. 6B which is a longitudinal cross-sectional view of tissue cooling module 21. Tissue cooling module 21 can assume a tubular, cylindrical configuration wherein tissue cooling module outer wall 22 and tissue cooling module inner wall 23 form tissue cooling module conduit 24 which is a lumen that is adapted to permit the flow of a cooling fluid through tissue cooling module 21 as depicted by the arrows in FIG. 6B. Tissue cooling module outer wall 22 and tissue cooling module inner wall 23 can be made from a thermal conductive material. Tissue cooling module outer wall 22 and tissue cooling module inner wall 23 can be made from the same or different materials. The material can be, for example, glass, steel, copper, aluminum, or combinations thereof. In some aspects, the material is a thermoelectric material, such as tellurium, for example. In some embodiments, tissue cooling module outer wall 22 is at least one of a Peltier cooler and printed circuit board. Tissue cooling module conduit 24 is in fluid communication with fluid pump 26 and fluid reservoir 25 through feed conduit 27 and return conduit 28. In embodiments where tissue cooling module 21 is detachably connected to laser system 1 by tip 3, tip 3 and laser system 1 comprise connectors adapted to provide a sealed connection between the portions of feed conduit 27 and return conduit 28 which are housed in laser system 1 and tip 3.

In function, fluid pump 26 draws a cooling fluid from fluid reservoir 25 and forces the fluid through feed conduit 27 into tissue cooling module conduit 24. The cooling fluid absorbs heat that is generated by the tissue of a patient and/or the application of laser 5 and/or laser 6 to the tissue, such heat being conducted to the cooling fluid through tissue cooling module outer wall 22 and tissue cooling module inner wall 23. The warmed cooling fluid returns to fluid reservoir 25 under the force of fluid pump 26 through return conduit 28. In some embodiments, cooling fan 31 is adapted to cool fluid reservoir 25 by drawing air into laser system 1 through at least one opening (not shown) in the system's housing and blowing the air against fluid reservoir 25 thereby dissipating heat from the fluid contained within fluid reservoir 25. Fluid reservoir 25 can be made from a thermal conductive material as disclosed herein.

In some embodiments, tissue cooling module conduit 24 is in fluid communication with a cooling system that is external to laser system 1. Tissue cooling module conduit 24 can be placed in fluid communication with the external cooling system by direct connection to tissue cooling module conduit 24, or through a connecting port that connects the external cooling system to fluid reservoir 25, fluid pump 26, feed conduit 27, or return conduit 28. Tissue cooling module conduit 24 can be in fluid communication with a system that is adapted to produce a flow of cold fluid, cold air or gas, or a combination thereof, through tissue cooling module conduit 24. The external system can be, for example a cold air device manufactured by Zimmer Medical Systems' (Irvine, CA).

In some aspects, the invention provides a method of treating a tissue with two or more beams of laser energy. In one embodiment, the method is practiced by providing laser system 1 as disclosed herein, and contacting a tissue with beams 5.1 and 6.1 simultaneously according to the beam the distribution patterns disclosed herein. Beams 5.1 and 6.1 can have the same or different wavexelengths and can have the same or different mode. The beam distribution patterns result in beams 5.1 and 6.1 contacting the tissue in a pattern selected from overlapping beams, partially overlapping beams, non-overlapping beams, and combinations thereof. Contacting the tissue with the beams causes the beams to propagate within the tissue in overlapping or spatially separated areas of the skin to produce zones of tissue damage leading the damaged tissues to release a cytokine profile into the surrounding, undamaged tissues. By contacting the tissue simultaneously and in spatially separated areas, beams 5.1 and 6.1 are prevented from interfering with one another since each beam contacts tissue that has not been damaged by laser light, it being understood that tissue that has been damaged by laser light can scatter and absorb a subsequent application of laser light and prevent the efficient propagation of the subsequent application of laser light within the tissue.

The method can comprise administering, simultaneously with the two or more beams of laser energy, at least one of ultrasound energy, microwave energy, and intense pulsed light. It is also contemplated that the method can comprise topically administering a composition during or after the application of laser energy. In some aspects, the composition is administered from within a reservoir in tip 3. The composition can be any composition that has a cosmetic or therapeutic effect on the skin condition being treated. Suitable compositions include, but are not limited to, drugs (e.g. Avastin™ and Lucentis™), anti-angiogenic antibodies, hyaluronic acid, Botox™ fibroblasts, stem cells, stem cell factors, vitamins, antioxidants, and combinations thereof.

In some aspects of the method, beams 5.1 and 6.1 propagate in the treated tissue in a pattern of overlapping beams, partially overlapping beams, non-overlapping beams, or combinations thereof. Beams 5.1 and 6.1 can also propagate at different depths. For example, beam 5.1 can propagate within the tissue at a depth that is shallower than the propagation of beam 6.1. For example, when laser system 1 is used to treat the skin, beam 5.1 can propagate only within the stratum corneum or epidermis, and beam 6.1 can propagate to a depth that reaches the papillary dermis or all dermal layers of the skin.

Beams 5.1 and 6.1 can have the same or different mode. The beams can be administered in a pulse beam mode, a continuous beam mode, or a combination thereof. The beams can have the same or different wavelengths, wherein the wavelengths are selected from about 540 nm, about 700 nm, about 810 nm, about 980 nm, about 1064 nm, about 1440 nm, about 1300 nm, about 1440 nm, about 1550 nm, about 1927 nm, about 1940 nm, about 2790 nm, about 2940 nm, about 10600 nm, about 1550 nm, and about 2790 nm.

In some embodiments, the invention provides a method of treating a tissue in a patient wherein cooling is applied to at least one of the treated tissue and the laser within laser system 1. In embodiments where cooling is applied to a tissue of a patient, tissue cooling module outer wall 22 of tissue cooling module 21 is contacted with the subject tissue and moved against the tissue to cause tissue cooling module 21 to rotate about its longitudinal axis. Heat is conducted from the contacted tissue through tissue cooling module outer wall 22 and tissue cooling module inner wall 23 and into a fluid flowing through tissue cooling module conduit 24. The heated cooling fluid flows from tissue cooling module conduit 24, through return conduit 28, and into fluid reservoir 25 through the action of fluid pump 26. The action of cooling fan 31 can dissipate heat from the heated cooling fluid within fluid reservoir 25 by blowing air against fluid reservoir 25.

Tissue cooling module 21 can be applied to cool the tissue of a patient at least one of before, during, and after the application of laser energy to the tissue of the patient. Cooling applied before laser therapy can increase the amount laser energy that can be applied to the tissue thereby permitting deeper penetration of laser energy, such as into the subcutaneous tissue of the skin for example, without pain and without damaging shallower tissue layers. Cooling of tissues after laser therapy can provide an anesthetic effect.

In at least one aspect, the method can be used to treat a skin condition. The skin condition can be any skin condition capable of being treated with two or more beams of laser energy. The skin condition can be wrinkles, loss of elasticity, skin photoaging, scars, rhytids, acne, telangiectasia, vitiligo, skin lesions, tattoo removal, blepharoptosis, or combinations thereof.

In one non-limiting embodiment, the invention provides a method of treating skin aging, wherein laser 5 comprises a laser diode that produces beam 5.1 in pulse mode at wavelength of about 1930 nm, and laser 6 produces beam 6.1 at a wavelength of about 1550 nm. A composition comprising at least one of vitamins, antioxidants, and stem cell factors is administered to the skin of the patient with or after the application of the laser energy. Without being limited to any particular theory or mechanism, the application of the laser energy perforates the skin permitting the composition to permeate the skin more efficiently. For example, the application of beam 5.1 can perforate the stratum corneum which would inhibit the absorption of the composition absent its perforation by beam 5.1. Beam 6.1 can increase the temperature of the deeper layers of the skin thereby enhancing the efficacy of the composition on the deeper layers of the skin.

In a further non-limiting embodiment, the method provides a method of treating rhytides, scars, or wrinkles in the skin. The method can be practiced by contacting the skin with a first laser beam having a wavelength of about 980 nm, a second laser beam having a wavelength of about 1440 nm, and a third laser beam having a wavelength of about 1930 nm. The first beam having a wavelength about 980 nm produces deep penetration of the skin. The second beam having wavelength of about 1440 propagates into the subcutaneous collagen. The third beam having a wavelength of about 1930 nm ruptures the stratum corneum. The beams can contact the skin in a pattern of overlapping beams, partially overlapping beams, non-overlapping beams, or combinations thereof. The beams can contact the skin in pulse mode, continuous mode, or a combination thereof. Contacting the skin with the beams can be performed simultaneously with, or before, the administration of a composition comprising Botox™, fibroblasts, stem cell factors, one or more skin fillers, or combinations thereof. The composition can be administered from a reservoir within tip 3.

It will be understood that in embodiments wherein three or more laser beams are administered, laser system 1 will comprise additional laser sources and scanners in optical communication with one another as disclosed herein, such that the additional laser sources are adapted to produce the beam distribution patterns disclosed herein.

In a further non-limiting embodiment, the invention provides a method for treating telangiectasia and pigmented lesions. This method can be practiced by contacting the skin with a first laser beam having wavelength of about 532 nm, a second laser beam having a wavelength of about 540 nm, and third laser beam having a wavelength of about 980 nm. The skin can be contacted with the beams in a pattern selected from overlapping beams, partially overlapping beams, non-overlapping beams, and combinations thereof. The beam having a wavelength of about 980 nm provides preheating of the skin and deep propagation of the beam within the skin, while the beams having wavelengths of about 532 nm and about 540 nm destroy the small blood vessels of the skin and have a shallow propagation within the skin. This embodiment of the method can comprise topically administering an antiangiogenic agent (e.g. Avastin™ or Lucentis™) simultaneously or after contacting the skin with the beams to inhibit the re-appearance of the destroyed blood vessels. The antiangiogenic agent can be administered from a reservoir within tip 3.

In a further non-limiting embodiment, the invention provides a method for treating pigmented lesions wherein a first laser beam having a wavelength of about 532 nm, a second laser beam having a wavelength of about 980 nm, and a third laser beam having a wavelength of about 1550 nm contact a skin having pigmented lesions.

In some embodiments, the system and method of the invention is used to treat tissues selected from corneal tissue, gastrointestinal epithelium, endothelial tissue, urothelium tissue, parenchymal tissue, respiratory tissue, connective tissue, cartilage, fat, and retinal tissue. It is further contemplated that the system and method of the invention can be used to treat kidney stones and gall stones, wherein one or more beams of laser energy are contacted with the kidney stones or gall stones.

While illustrative embodiments of the invention have been described herein, the present invention is not limited to the various preferred embodiments described herein, but includes any and all embodiments having equivalent elements, modifications, omissions, combinations (e.g. of aspects across various embodiments), adaptations and/or alterations as would be appreciated by those in the art based on the present disclosure. The limitations in the claims are to be interpreted broadly based on the language employed in the claims and not limited to the examples described in the present specification or during prosecution of the application, which examples are to be construed as non-exclusive. Unless dictated otherwise by context, like reference numbers refer to the same features as described throughout the specification and depicted in the accompanying drawings.

The invention claimed is:

1. A laser system for treating a tissue in a patient, comprising a handpiece having at least one laser that is adapted to treat said tissue, wherein said handpiece includes:
   a) a tissue cooling module that is adapted to cool said tissue, wherein said tissue cooling module comprises (i) a tubular body having a longitudinal axis, wherein said tubular body (A) comprises an inner wall that forms a lumen within said tubular body, and (B) is adapted to rotate about said longitudinal axis when said tubular body is moved against a tissue of a patient, (ii) a feed conduit in fluid communication with a reservoir, wherein said feed conduit is adapted to conduct a fluid from said reservoir to said lumen, (iii) a return conduit adapted to receive said fluid from said lumen, wherein said return conduit is in fluid communication with said reservoir and is adapted to return said fluid from said lumen to said reservoir; (iv) a pump that is in-line with said feed conduit, wherein said pump is adapted to (C) force said fluid from said reservoir through said feed conduit and said lumen, and (D) return said fluid to said reservoir through said return conduit; and
   b) at least one laser cooling module that is adapted to cool said at least one laser;
   wherein said tubular body comprises an outer wall that is free of apertures and is made of a non-transparent material.

2. The laser system of claim 1, wherein said handpiece comprises a plurality of lasers.

3. The laser system of claim 1, wherein said at least one laser cooling module comprises at least one of: (i) one or more printed circuit boards; (ii) one or more Peltier coolers; and (iii) one or more thermoelectric plates.

4. The laser system of claim 1, wherein said at least one laser cooling module is in thermal communication with a thermal sink.

5. The laser system of claim 4, wherein said thermal sink is in communication with a fan that is adapted to simultaneously dissipate heat from said thermal sink and said reservoir.

6. The laser system of claim 1, wherein said tubular body comprises at least one of a Peltier cooler, a thermoelectric material and a printed circuit board.

7. The laser system of claim 1, wherein said outer wall comprises at least one of a Peltier cooler, a thermoelectric material and a printed circuit board.

8. The laser system of claim 1, wherein said tubular body is connected to a detachable tip or is fixed to a housing that encloses said handpiece.

9. The laser system of claim 1, wherein said non-transparent material is steel, copper, aluminum, or a combination thereof.

10. A laser system for treating a tissue in a patient, comprising
   a) a handpiece having at least one laser that is adapted to treat tissue,
   b) a tissue cooling module that is adapted to cool tissue on a patient, wherein said tissue cooling module comprises (i) a tubular body having a longitudinal axis, wherein said tubular body (A) comprises an inner wall that forms a lumen within said tubular body, and (B) is adapted to rotate about said longitudinal axis when said tubular body is moved against a tissue of a patient, (ii) a feed conduit in fluid communication with a reservoir, wherein said feed conduit is adapted to conduct a fluid from said reservoir to said lumen, (iii) a return conduit adapted to receive said fluid from said lumen, wherein said return conduit is in fluid communication with said reservoir and is adapted to return said fluid from said lumen to said reservoir, and (iv) a pump that is in-line with said feed conduit, wherein said pump is adapted to (C) force said fluid from said reservoir through said feed conduit and said lumen, and (D) return said fluid to said reservoir through said return conduit, wherein said tubular body comprises an outer wall that is free of apertures and made of a non-transparent material;
   c) at least one laser cooling module that is adapted to cool said at least one laser;
   d) a thermal sink in thermal communication with said at least one laser cooling module; and
   g) a fan that is adapted to simultaneously dissipate heat from said thermal sink and said reservoir.

* * * * *